US011164660B2

(12) United States Patent
Smith

(10) Patent No.: US 11,164,660 B2
(45) Date of Patent: Nov. 2, 2021

(54) VISUALLY AUGMENTING A GRAPHICAL RENDERING OF A CHEMICAL STRUCTURE REPRESENTATION OR BIOLOGICAL SEQUENCE REPRESENTATION WITH MULTI-DIMENSIONAL INFORMATION

(71) Applicant: PerkinElmer Informatics, Inc., Waltham, MA (US)

(72) Inventor: Robin Y. Smith, Boston, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 0 days.

(21) Appl. No.: 14/471,456

(22) Filed: Aug. 28, 2014

(65) Prior Publication Data
US 2015/0112604 A1    Apr. 23, 2015

Related U.S. Application Data

(63) Continuation of application No. 14/058,865, filed on Oct. 21, 2013, now Pat. No. 8,854,361.
(Continued)

(51) Int. Cl.
*G16B 5/00* (2019.01)
*G06T 19/00* (2011.01)
(Continued)

(52) U.S. Cl.
CPC ............... *G16B 45/00* (2019.02); *G06F 3/14* (2013.01); *G06T 19/006* (2013.01); *G09B 5/02* (2013.01);
(Continued)

(58) Field of Classification Search
CPC ......... G06F 3/14; G06F 9/006; G06T 19/006; G09B 5/02; G09G 2340/10;
(Continued)

(56) References Cited

U.S. PATENT DOCUMENTS 4,967,372 A    10/1990  Feldman
5,008,831 A     4/1991  Feldman
(Continued)

FOREIGN PATENT DOCUMENTS

EP    1526471 A1    4/2005
EP    1613009 A1    1/2006
(Continued)

OTHER PUBLICATIONS

Harris, "Genotator: A Workbench for Sequence Annotation", Genome Research, v. 7, pp. 754-762, 1997.*
(Continued)

*Primary Examiner* — Jennifer N To
*Assistant Examiner* — Reji Kartholy
(74) *Attorney, Agent, or Firm* — Banner & Witcoff, Ltd.

(57) ABSTRACT

In certain embodiments, the invention relates to systems, methods, and apparatus that allow a user to visually augment a graphical rendering of either a chemical structure representation or a biological sequence representation with multi-dimensional information. A user captures a video image using a computing device such as a hand-held smart phone, computerized eye glasses or tablet computer. The video image includes information regarding at least one of a chemical structure and a biological sequence. A processor identifies, within the video image, a graphical representation of at least one of a chemical structure and a biological structure. The processor augments the graphical representation with additional information and provides the video data for presentation upon a display controlled by the computing device. The computing device presents the video data in substantially real time in relation to the capture of the video data by the computing device.

22 Claims, 6 Drawing Sheets

Related U.S. Application Data

(60) Provisional application No. 61/779,607, filed on Mar. 13, 2013.

(51) Int. Cl.
*G16C 10/00* (2019.01)
*G16B 45/00* (2019.01)
*G09B 5/02* (2006.01)
*G06F 3/14* (2006.01)
*G16C 20/80* (2019.01)

(52) U.S. Cl.
CPC .............. *G16B 5/00* (2019.02); *G16C 10/00* (2019.02); *G16C 20/80* (2019.02); *G09G 2340/10* (2013.01); *G09G 2370/022* (2013.01); *G09G 2380/08* (2013.01)

(58) Field of Classification Search
CPC ......... G09G 2370/022; G09G 2380/08; G16B 5/00; G16B 45/00; G16C 10/00; G16C 20/80
See application file for complete search history.

(56) References Cited

U.S. PATENT DOCUMENTS

| | | | |
|---|---|---|---|
| 5,025,388 A * | 6/1991 | Cramer, III | C07K 1/00 700/293 |
| 5,249,137 A | 9/1993 | Wilson et al. | |
| 5,307,287 A * | 4/1994 | Cramer, III | C07K 1/00 703/2 |
| 5,345,516 A * | 9/1994 | Boyer | G06K 9/00476 382/113 |
| 5,386,507 A | 1/1995 | Teig et al. | |
| 5,394,455 A * | 2/1995 | Roeck | A61B 6/464 348/E5.086 |
| 5,434,971 A | 7/1995 | Lysakowski, Jr. | |
| 5,461,580 A | 10/1995 | Facci et al. | |
| 5,517,237 A * | 5/1996 | Cocanour, III | F27D 21/02 266/80 |
| 5,555,366 A * | 9/1996 | Teig | G06T 17/00 345/419 |
| 5,902,732 A * | 5/1999 | Hochman | G01N 33/6896 435/288.7 |
| 5,920,317 A * | 7/1999 | McDonald | G01S 7/52073 715/853 |
| 5,993,001 A * | 11/1999 | Bursell | G06F 19/321 351/212 |
| 6,006,241 A * | 12/1999 | Purnaveja | H04N 5/04 715/205 |
| 6,017,390 A | 1/2000 | Charych et al. | |
| 6,078,681 A * | 6/2000 | Silver | G01N 21/6428 250/461.2 |
| 6,154,771 A * | 11/2000 | Rangan | H04N 5/76 709/217 |
| 6,169,840 B1 * | 1/2001 | Lemelson | B07C 5/10 386/201 |
| 6,304,869 B1 | 10/2001 | Moore et al. | |
| 6,434,490 B1 | 8/2002 | Agrafiotis et al. | |
| 6,449,653 B2 * | 9/2002 | Klemets | H04L 29/06 348/423.1 |
| 6,582,233 B1 | 6/2003 | Clark | |
| 6,973,616 B1 * | 12/2005 | Cottrille | G06F 16/957 715/234 |
| 7,043,415 B1 * | 5/2006 | Dunlavey | G06F 19/708 702/19 |
| 7,250,950 B2 | 7/2007 | Smith et al. | |
| 7,613,574 B2 | 11/2009 | Verseput | |
| 7,650,327 B2 | 1/2010 | Remsen et al. | |
| 7,663,607 B2 | 2/2010 | Hotelling et al. | |
| 7,676,499 B2 | 3/2010 | Dorsett, Jr. | |
| 7,705,830 B2 | 4/2010 | Westerman et al. | |
| 7,707,206 B2 | 4/2010 | Encina et al. | |
| 7,805,437 B1 | 9/2010 | Andersson et al. | |
| 7,912,689 B1 | 3/2011 | Helson | |
| 8,139,650 B2 * | 3/2012 | Cunha | H04N 19/80 375/240.29 |
| 8,296,670 B2 | 10/2012 | Matthews et al. | |
| 8,407,578 B2 | 3/2013 | Boyer et al. | |
| 8,433,723 B2 | 4/2013 | Smith et al. | |
| 8,443,279 B1 * | 5/2013 | Hameed | A61B 1/00041 715/230 |
| 8,854,361 B1 | 10/2014 | Smith | |
| 9,031,977 B2 * | 5/2015 | Smith | G06F 19/705 707/769 |
| 9,430,127 B2 | 8/2016 | Smith et al. | |
| 9,535,583 B2 | 1/2017 | Smellie et al. | |
| 2002/0049548 A1 | 4/2002 | Bunin | |
| 2002/0051999 A1 | 5/2002 | Sepetov et al. | |
| 2002/0107359 A1 | 8/2002 | Hogarth et al. | |
| 2002/0161599 A1 | 10/2002 | Faerman et al. | |
| 2002/0169564 A1 * | 11/2002 | Delaney | G06F 19/26 702/20 |
| 2003/0194687 A1 | 10/2003 | Clark | |
| 2004/0003000 A1 | 1/2004 | Smith et al. | |
| 2004/0006742 A1 | 1/2004 | Slocombe | |
| 2004/0024493 A1 | 2/2004 | Fagrell et al. | |
| 2004/0068758 A1 * | 4/2004 | Daily | H04N 7/17318 725/136 |
| 2004/0088118 A1 | 5/2004 | Jensen et al. | |
| 2004/0101876 A1 * | 5/2004 | Mintz | G06F 19/12 435/6.12 |
| 2004/0122641 A1 | 6/2004 | Miller et al. | |
| 2004/0171062 A1 | 9/2004 | Hirth et al. | |
| 2004/0172593 A1 * | 9/2004 | Wong | G06F 16/40 715/201 |
| 2004/0221227 A1 * | 11/2004 | Wu | G11B 27/034 715/202 |
| 2004/0236740 A1 | 11/2004 | Cho et al. | |
| 2004/0249791 A1 | 12/2004 | Waters et al. | |
| 2005/0010603 A1 | 1/2005 | Berks | |
| 2005/0094205 A1 | 5/2005 | Lo et al. | |
| 2005/0102313 A1 | 5/2005 | Levering et al. | |
| 2005/0123993 A1 | 6/2005 | Brunner et al. | |
| 2005/0131894 A1 | 6/2005 | Vuong | |
| 2005/0177280 A1 | 8/2005 | Almstetter et al. | |
| 2005/0203898 A1 | 9/2005 | Boyer et al. | |
| 2005/0212759 A1 | 9/2005 | Marvit et al. | |
| 2005/0226495 A1 | 10/2005 | Li | |
| 2005/0259882 A1 * | 11/2005 | Dewaele | G06T 7/75 382/243 |
| 2006/0040322 A1 | 2/2006 | Archetti et al. | |
| 2006/0061595 A1 | 3/2006 | Goede et al. | |
| 2006/0068405 A1 * | 3/2006 | Diber | C07K 14/705 435/6.14 |
| 2006/0123113 A1 | 6/2006 | Friedman | |
| 2006/0277201 A1 | 12/2006 | Dorsett | |
| 2007/0016853 A1 | 1/2007 | Abagyan et al. | |
| 2007/0031062 A1 * | 2/2007 | Pal | H04N 5/23238 382/284 |
| 2007/0146347 A1 | 6/2007 | Rosenberg | |
| 2007/0174765 A1 | 7/2007 | Schleppenbach et al. | |
| 2007/0177803 A1 | 8/2007 | Elias et al. | |
| 2007/0192747 A1 | 8/2007 | Phelan et al. | |
| 2007/0250299 A1 * | 10/2007 | Paxson | G06F 19/26 703/11 |
| 2007/0260583 A1 | 11/2007 | Domine et al. | |
| 2007/0276636 A1 | 11/2007 | Wythoff | |
| 2008/0004810 A1 * | 1/2008 | Boyer | G06F 19/705 702/19 |
| 2008/0036743 A1 | 2/2008 | Westerman et al. | |
| 2008/0136785 A1 | 6/2008 | Baudisch et al. | |
| 2008/0140616 A1 | 6/2008 | Encina et al. | |
| 2008/0165140 A1 | 7/2008 | Christie et al. | |
| 2008/0213663 A1 | 9/2008 | Hu et al. | |
| 2008/0228774 A1 | 9/2008 | Hamilton et al. | |
| 2008/0234135 A1 * | 9/2008 | Ghosh | G06F 19/706 506/2 |
| 2008/0234996 A1 * | 9/2008 | Ghosh | G06F 19/706 703/12 |
| 2008/0309632 A1 | 12/2008 | Westerman et al. | |

(56) References Cited

U.S. PATENT DOCUMENTS

| | | |
|---|---|---|
| 2009/0006411 A1 | 1/2009 | Lele et al. |
| 2009/0063427 A1 | 3/2009 | Zuta et al. |
| 2009/0125544 A1* | 5/2009 | Brindley ............... G06F 3/0487 |
| 2009/0171975 A1 | 7/2009 | McConnell et al. |
| 2009/0244015 A1 | 10/2009 | Sengupta et al. |
| 2009/0273571 A1 | 11/2009 | Bowens |
| 2009/0288044 A1 | 11/2009 | Matthews et al. |
| 2009/0298114 A1* | 12/2009 | Courtney ........... G01N 21/6458 435/29 |
| 2010/0079369 A1 | 4/2010 | Hartmann et al. |
| 2010/0137027 A1 | 6/2010 | Kim |
| 2010/0156812 A1 | 6/2010 | Stallings et al. |
| 2010/0241691 A1* | 9/2010 | Savitzky ................ G06F 15/16 709/203 |
| 2010/0257457 A1 | 10/2010 | De Goes |
| 2011/0055696 A1 | 3/2011 | Dollar et al. |
| 2011/0072339 A1* | 3/2011 | Boyer ................... G06F 17/241 715/212 |
| 2011/0163944 A1 | 7/2011 | Bilbrey et al. |
| 2011/0164163 A1* | 7/2011 | Bilbrey ................. G06F 1/1694 348/333.01 |
| 2011/0221656 A1 | 9/2011 | Haddick et al. |
| 2011/0276589 A1 | 11/2011 | Smith et al. |
| 2012/0019488 A1 | 1/2012 | McCarthy |
| 2012/0078853 A1 | 3/2012 | Huang et al. |
| 2012/0109972 A1* | 5/2012 | Boyer .................. G06F 19/705 707/748 |
| 2012/0110486 A1 | 5/2012 | Sirpal et al. |
| 2012/0154440 A1 | 6/2012 | Nicholls et al. |
| 2012/0173622 A1 | 7/2012 | Toledano et al. |
| 2012/0185513 A1 | 7/2012 | Samukawa |
| 2012/0188147 A1 | 7/2012 | Hosein et al. |
| 2012/0216153 A1 | 8/2012 | Sip |
| 2012/0226150 A1* | 9/2012 | Balicki ................. A61B 5/0066 600/424 |
| 2012/0246228 A1 | 9/2012 | Udezue et al. |
| 2012/0249580 A1* | 10/2012 | Schwartz ................ G06F 19/18 345/629 |
| 2012/0284638 A1 | 11/2012 | Cutler et al. |
| 2012/0311038 A1 | 12/2012 | Trinh et al. |
| 2012/0324368 A1 | 12/2012 | Putz et al. |
| 2013/0044042 A1 | 2/2013 | Olsson et al. |
| 2013/0061163 A1 | 3/2013 | Clark et al. |
| 2013/0218878 A1 | 8/2013 | Smith et al. |
| 2013/0222265 A1 | 8/2013 | Smith et al. |
| 2013/0297058 A1 | 11/2013 | Griffith et al. |
| 2013/0311868 A1* | 11/2013 | Monney ................. G06T 11/60 715/230 |
| 2013/0314441 A1* | 11/2013 | Grasset .................. G06T 1/00 345/633 |
| 2014/0042670 A1 | 2/2014 | Pettis et al. |
| 2014/0046643 A1* | 2/2014 | Paxson ................. G06F 19/26 703/12 |
| 2014/0046696 A1* | 2/2014 | Higgins ................. G06F 19/345 705/3 |
| 2014/0082015 A1 | 3/2014 | Huang et al. |
| 2014/0089329 A1 | 3/2014 | Kozloski et al. |
| 2014/0173475 A1 | 6/2014 | Smellie et al. |
| 2014/0173476 A1 | 6/2014 | Smellie et al. |
| 2014/0267240 A1 | 9/2014 | Smith |
| 2014/0267723 A1* | 9/2014 | Davidson, Jr. .......... G06T 17/05 348/147 |
| 2014/0282106 A1 | 9/2014 | Smith et al. |
| 2014/0301608 A1* | 10/2014 | Karthikeyan ...... G06K 9/00476 382/113 |
| 2014/0336807 A1 | 11/2014 | Smith et al. |
| 2014/0337725 A1 | 11/2014 | Smith et al. |
| 2015/0051889 A1* | 2/2015 | Ohrn .................... G06F 19/708 703/2 |
| 2015/0142730 A1 | 5/2015 | Dakshanamurthy et al. |
| 2015/0199797 A1 | 7/2015 | Palo |

FOREIGN PATENT DOCUMENTS

| | | | |
|---|---|---|---|
| EP | 2224389 A1 | 9/2010 | |
| GB | 2493830 A | 2/2013 | |
| WO | WO-01/0803 A2 | 2/2001 | |
| WO | WO-2007092842 A2 | 8/2007 | |
| WO | WO-2011/041427 A2 | 4/2011 | |
| WO | WO-2011/140148 A1 | 11/2011 | |
| WO | WO-2012/068548 A1 | 5/2012 | |
| WO | WO 2013/030850 A2 * | 3/2013 | ......... G06K 9/00476 |
| WO | WO-2013/126077 A1 | 8/2013 | |

OTHER PUBLICATIONS

Harris, "Annotating Sequence Data Using Genotator", Molecular Biotechnology, v. 16, pp. 221-232, 2000.*

Wall et al., "Genotator: A disease-agnostic tool for genetic annotation of disease", BMC Medical Genomics, v. 3, n. 50, pp. 1-10, 2010.*

Lamprecht et al., "CellProfiler™: free, versatile software for automated biological image analysis", BioTechniques, v. 42, n. 1, pp. 71-75, Feb. 2007.*

Peng et al., "Automatic image analysis for gene expression patterns of fly embryos", BMC Cell Biology, v. 8, Suppl. 1, pp. 1-13, Jul. 2007.*

Saalfeld et al., "CATMAID: collaborative annotation toolkit for massive amounts of image data", v. 25, n. 15, pp. 1984-1986, Apr. 2009.*

"Columbus System: Image Data Management and Analysis System" brochure, PerkinElmer, Jun. 2010.*

"Volocity Software: 3D Image Analysis Software" brochure, PerkinElmer, Sep. 2011.*

Algorri et al., Reconstruction of Chemical Molecules from Images, 2007 Annual International Conference of the IEEE Engineering in Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.

Australian Patent Application No. 2011248243, APO Examination Report No. 1, dated Nov. 5, 2013, 3 pages.

Bennett, Samsung's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.

Carmigniani, J. et al., Augmented Reality Technologies, Systems and Applications, Multimedia Tools and Applications 51:341-377, (2011).

Casey et al., Optical Recognition of Chemical Graphics, Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.

Chinese First Office Action, Application No. 201190000597.X, dated May 29, 2013, 4 pages Including Translation.

Clark A. M., Basic Primitives for Molecular Diagram Sketching, Journal of Cheminformatics 2:8 (2010).

European Search Report for 13275308.8, dated Apr. 9, 2014, 4 pages.

European Search Report for 13275308.8, dated Aug. 13, 2014, 8 pages.

Filippov et al., Optical Structure Recognition Software to Recover Chemical Information: OSRA, An Open Source Solution, Journal of Chemical Information and Modeling, vol. 49, No. 3, Mar. 23, 2009, pp. 740-743.

Flick—Simply the easiest way to share, <http://getflick.io/> [retrieved Aug. 23, 2013], 4 pages.

Furlon, Rod, Build Your Own Google Glass, Resources Hands On, IEEE Spectrum, IEEE Inc., vol. 50, No. 1, pp. 20-21, (Jan. 1, 2013).

Giudice N. A. et al., Learning Non-Visual Graphical Information Using a Touch-Based Vibro-Audio Interface, Proceedings of the 14th International ACM Sigaccess Conference on Computers and Accessibility, Assets '12, 103-110 (Jan. 1, 2012).

(56) References Cited

OTHER PUBLICATIONS

Gonzalez-Villanueva et al., WallShare: A Collaborative Multi-pointer System for Portable Devices, Nov. 19, 2012, 7 pages.
International Search Report for PCT/US2011/035070, dated Oct. 6, 2011, 4 pages.
International Search Report for PCT/US2011/061534, dated Mar. 16, 2012, 2 pages.
International Search Report for PCT/US2012/026574, dated Mar. 20, 2013, 4 pages.
International Search Report for PCT/US2014/015131, dated Aug. 21, 2014, 6 pages.
International Search Report for PCT/US2014/016249, dated Aug. 13, 2014, 4 pages.
International Search Report for PCT/US2014/035685, dated Aug. 4, 2014, 4 pages.
ITunes Preview, Flick for iPhone, iPad, and iPod touch on the iTunes App Store, <https://itunes.apple.com/us/app/flicklid644265534?mt=8> [retrieved Oct. 28, 2013], 2 pages.
Jurach, T., Microsoft Outlook Quick Start Email Guide!, 1-3 (2006).
Kim et al., Development of a Gesture-Based Molecular Visualization Tool Based on Virtual Reality for Molecular Docking, Bull. Korean Chem. Soc. 2004, vol. 25, No. 10, pp. 1571-1574.
Layar, What is Layar?, <http://www.layar.com/features/> [retrieved Nov. 14, 2012], 7 pages.
Li et al., Personal Experience with Four Kinds of Chemical Structure Drawing Software: Review on ChemDraw, ChemWindow, ISIS/Draw, and ChemSketch, J. Chem. Inf. Comput. Sci. 44:1886-1890 (2004).
Lorensen et al., Marching Cubes: A high resolution 3D surface construction algorithm. In: Computer Graphics, vol. 21, Nr. 4, Jul. 1987.
Lucero et al., Pass-Them-Around: Collaborative Use of Mobile Phones for Photo Sharing, CHI 2011—Session: Photo Sharing, May 7-11, 2011, Vancouver, BC, Canada, 10 pages.
Park et al., Automated Extraction of Chemical Structure Information From Digital Raster Images, Chemistry Central Journal, Biomed Central Ltd., vol. 3, No. 1, Feb. 5, 2009, pp. 1-16.
Park et al., Tunable Machine Vision-Based Strategy for Automated Annotation of Chemical Databases, Journal of Chemical Information and Modeling, vol. 49, No. 8, 2009, pp. 1993-2001.
Pering et al., Enabling Pervasive Collaboration with Platform Composition, Intel Research Santa Clara, 2009, 18 pages.
Pering et al., Spontaneous Marriages of Mobile Devices and Interactive Spaces, Communications of the ACM, Sep. 2005, vol. 48, No. 9, pp. 53-59, 7 pages.
Scheible et al., MobiToss: A Novel gesture based interface for creating and sharing mobile multimedia art on large public displays, MM'08, Oct. 26-31, 2008 Vancouver British Columbia, Canada, pp. 957-960, 4 pages.
Shine et al., ChemPad3 a tutorial, May 21, 2008, 10 pages.
Toennies J. L. et al., Toward Haptic/Aural Touchscreen Display of Graphical Mathematics for the Education of Blind Students, WHC, IEEE, 373:378 (2011).
Tsotsis, Word Lens Translates Words Inside of Images. Yes Really., <http://techcrunch.com/2010/12/16/world-lens-translates-words-inside-of-images-yes-really/> [retrieved Nov. 14, 2012], Dec. 16, 2010, 3 pages.
Valko et al., CLiDE Pro: The Latest Generation of CLiDE, a Tool for Optical Chemical Structure Recognition, Journal of Chemical Information and Modeling, vol. 94, No. 4, Apr. 27, 2009, pp. 780-787.
Weinberg et al., ZooZBeat: a Gesture-based Mobile Music Studio, NIME 2009, pp. 312-315, 4 pages.
Williams et al., Mobile apps for chemistry in the world of drug discovery, Drug Discovery Today, vol. 16. No. 21/22, Nov. 2011, pp. 928-939.
Williams et al., Smart Phones, a Powerful Tool in the Chemistry Classroom, Journal of Chemical Education, 2011, pp. 683-686.
Wobbrock et al., User-Defined Gestures for Surface Computing, CHI—Tabletop Gestures, Apr. 7, 2009, pp. 1083-1092.
Written Opinion for PCT/US2011/035070, dated Oct. 6, 2011, 9 pages.
Written Opinion for PCT/US2011/061534, dated Mar. 16, 2012, 5 pages.
Written Opinion for PCT/US2012/026574, dated Mar. 20, 2013, 8 pages.
Written Opinion for PCT/US2014/015131, dated Aug. 21, 2014, 10 pages.
Written Opinion for PCT/US2014/016249, dated Aug. 13, 2014, 7 pages.
Written Opinion for PCT/US2014/035685, dated Aug. 4, 2014, 8 pages.
"Introduction to Drawing (iPhone)", http://molmatinf.com/introdrawios.html, Molecular Materials Informatics, Inc., Dec. 9, 2010, retrieved by Archive.org as https://web.archive.org/web/20120413131358/http:I/molmatinf.com/introdrawios.html on Apr. 13, 2012.
"Overview of Drawing Gestures (iPhone)", http://molmatinf.com/gesturesios.html, Molecular Materials Informatics, Inc., Nov. 3, 2010, retrieved by Archive.org as https://web.archive.org/web/20101118005114/http:I/molmatinf.com/gesturesios.html on Nov. 18, 2010.
Cambridgesoft, Inc., Chem & Bio Draw, Version 12.0, 24 pages, 2009.
Cambridgesoft, Inc., ChemDraw User's Guide, Version 9.0.1, 23 pages, 2004.
ChemJuice Grande—Basic Structure Drawing, printout page of YouTube video posting from IOBS at http://www.youtube.com/watch?v=mKOcC5bLzdO, <http://www.youtube.com/watch?v=mKOcC5bLzdO>uploaded Oct. 3, 2011, printed May 18, 2015, 2 pages.
IDBS Makes Chemical Structure Drawing Mobile, Press Release, ID Business Solutions, Ltd., 2 pages, Dec. 9, 2009.
Logtenberg, Jeroen, Multi-user interaction with molecular visualizations on a multi-touch table, MSc thesis, Human Media Interaction Group, University of Twente, 48 pages, Aug. 11, 2009.
Mills, Nancy, ChemDraw Ultra 10.0, Journal of American Chemical Society, 128(41):13649-13650, 2006.
Mobile Molecular DataSheet, http://molmatinf.com/mmdsios.html, <http://molmatinf.com/mmdsios.html>Molecular Materials Informatics, Inc., Sep. 23, 2011, retrieved by Archive.org as https://web.archive.org/web/20120403140454/http:I/molmatinf.com/mmdsios.html on Apr. 3, 2012, 4 pages.
MoiPrime+, http://molmatinf.com/molprimeplus.html, <http://molmatinf.com/molprimeplus.html>Molecular Materials Informatics, Inc., Jan. 23, 2011, 13 pages.
Chemistry World, Mobile chemistry—chemistry in your hands and face, 21 pages (2010), retrieved on Feb. 23, 2017,www.chemistryworld.com/opinion/comment/1014923.article>, paragraphs [0019] and [0020] and fig. 1.
Jenny. 3D-Printed Enzyme—Proof of Concept, retrieved Jan. 17, 2017 from <https://caretdashcaret.com/2012/10/31/3d-printed-enzyme-proof-of-contept>, 5 pages (2012).
Kawakami, M., A soft and transparent handleable protein model, Review of Scientific Instruments 83:084303-1-7 (2012).
Phlegmatic prototyping, 6 pages (2012), retrieved Jan. 17, 2017 from <http://phlegmatic-protyting.tumblr.com/post/20488949350/printing-a-molecule-part-1>.
Waterman, P. J., Preparing 3D Models, 6 pages (2012), retrieved Jan. 17, 2017 from <http://www.digitaleng.news/de/preparing-3d-models/>.
Williams, A. J. et al., Mobile apps for chemistry in the world of drug discovery, Drug Discovery Today, 16(21/22):928-939 (2011).
Klekota, J. et al., Query Chem: a Google-powered web search combining text and chemical structures, Bioinformatics Applications Note, 22(13):1670-1673 (2006).
Textco Biosoftware, Inc., Gene Inspector 2.0 Tutorials and User Manual, 24 pages (2012).
Tönnies, S. et al., Taking Chemistry to the Task—Personalized Queries for Chemical Digital Libraries, Digital Libraries, ACM, pp. 325-334 (2011).
Various Authors: Chemical Database—Wikipedia, Wikipedia on line encyclopedia, [retrieved from the Internet: URL:https://en.

(56) References Cited

OTHER PUBLICATIONS wikipedia.org/w/index.php?title=Chemical_database&oldid=732531151 [retrieved on Oct. 16, 2017] pp. 1-6 (2016).
May 30, 2018—(EP) Office Action—App 14708174.9.
Feb. 27, 2019—(EP) Office Action—App 14708174.9.
Nov. 27, 2019—(EP) Office Action—App 14708174.9.
Jul. 10, 2019—(EP) Office Action—App 14708174.9.
May 11, 2020—(EP) Notice of Allowance—App No. 14708174.9.
"Identifying, Indexing, and Ranking Chemical Formulae and Chemical Names in Digital Text." Cetintas et al. Purdue University. Available from [https://www.cs.purdue.edu/homes/lsi/Federated_Search/IR_slides.htm] (last modified May 7, 2012) and [https://www.cs.purdue.edu/homes/lsi/Federated_Search/IR_for_Chemistry.pdf].

* cited by examiner

VISUALLY AUGMENTING A GRAPHICAL RENDERING OF A CHEMICAL STRUCTURE REPRESENTATION OR BIOLOGICAL SEQUENCE REPRESENTATION WITH MULTI-DIMENSIONAL INFORMATION

RELATED APPLICATIONS

The present application is a Continuation of U.S. Non-Provisional application Ser. No. 14/058,865 entitled "Visually Augmenting a Graphical Rendering of a Chemical Structure Representation or Biological Sequence Representation with Multi-Dimensional Information," filed Oct. 21, 2013, which claims priority to and the benefit of, U.S. Provisional Application No. 61/779,607 entitled "Visually Augmenting a Graphical Rendering of a Chemical Structure Representation or Biological Sequence Representation with Multi-Dimensional Information," filed Mar. 13, 2013, the contents of both of which are hereby incorporated by reference in their entirety.

BACKGROUND

Chemical structure rendering software is widely used by research and educational institutions to depict chemical structures and chemical reactions of interest. Unlike chemical formulas or chemical names, structural formulas provide a graphical representation of the molecular structure. A graphical chemical structure representation is capable of indicating the arrangements of atoms in a way that a chemical formula cannot.

Biological sequence and large molecule rendering software is widely used by research and educational institutions to depict biological sequences, including nucleotide and amino acid sequences of interest. A three-dimensional graphical representation can be extrapolated from a nucleotide and/or amino acid sequence to depict the arrangements of atoms, nucleotides, and/or amino acid residues in a way that a simple sequence (e.g., a nucleotide and/or amino acid sequence) cannot.

Augmented reality refers to augmenting the real world environment with computer-generated input such as graphics, video, or audio information. In handheld device augmented reality, digital objects can be overlaid on real world video data captured on the handheld computing device. Examples of handheld device augmented reality include the Layar™ print media augmentation application by Layar of Amsterdam, the Netherlands, the Word Lens augmented reality translation application by Quest Visual of San Francisco, Calif., and the Wikitude® Augmented Reality mobile platform by Wikitude GmbH of Salzburg, Austria.

SUMMARY OF THE INVENTION

Described herein are various embodiments of systems, methods, and apparatus that allow a user to visually augment a graphical rendering of either a chemical structure representation or a biological sequence representation with multi-dimensional information. Initially, using a computing device such as a hand-held smart phone, computerized eye glasses or tablet computer, a user captures a video image containing information regarding at least one of a chemical structure and a biological sequence. In one example, the video image may capture an illustration of a chemical structure, such as a two-dimensional rendering of a chemical structure drawn on a piece of paper, white board, chalk board, or transparent drawing board as in a laboratory. Instead of a graphical rendering of a chemical structure, in another example, the video image may capture a written chemical name, biological species name, formula, or other visual indication of a chemical compound or biological species.

In an example embodiment, the computing device used to capture the video image accesses software configured to identify the captured chemical structure or biological sequence. The software is further configured to augment the video image, prior to being displayed to the user (e.g., in a display area of the computing device or on a separate display), with information regarding the captured chemical structure or biological sequence. The information, in some examples, can include the chemical name, biological species name, properties of the chemical compound or biological species, whether the identified chemical compound or biological species is available in a given lab or stock room, and (if identified in a lab or stock room) a storage location of the identified chemical compound or biological species. In another example, the information can include a three-dimensional representation of the chemical structure or biological sequence.

The display containing the augmented video image, in a preferred embodiment, is presented in substantially real-time, such that the video is captured, augmented with additional information pertaining to a chemical structure or biological sequence rendered therein, and displayed to the user while the user continues to capture the video image containing the image of the chemical structure or biological sequence. The additional information, for example, may be positionally linked to the captured image of the chemical structure or biological sequence (or other graphical representation) being viewed. For example, the additional information may be superimposed on, or placed in proximity to, the video image of a two-dimensional graphical chemical structure captured within the video image.

Call-out boxes may be displayed on the screen prompting the user to choose to display particular additional information such as, in some examples, the name, storage location, and/or properties of the identified chemical structure or biological species. The call-out boxes, for example, may be superimposed on the live video image being viewed such that it is clear to the user what portion of the captured video image has been identified by the software as a chemical structure or biological sequence. For example, the additional information may be displayed (i) on top of the video image of an identified graphical rendering of a chemical structure or biological sequence, (ii) in a call-out box pointing to the identified graphical rendering of the chemical structure or biological sequence, or (iii) superimposed on top of (e.g., at least partially overlapping) the identified graphical rendering of the chemical structure or biological sequence. The additional information, in some embodiments, is rendered partially transparent such that the captured video image is visible beneath the additional information. The additional information, in this circumstance, may optionally be rendered opaque responsive to selection by a user (e.g., receiving a touch input corresponding to a transparent call-out box rendered upon a touch screen device, etc.). If multiple chemical structure representations and/or biological sequence representations are identified, the position of the additional information (or displayed information prompts), in some embodiments, indicates which identified chemical structure or biological sequence correlates to which additional information.

A three-dimensional representation of the identified chemical structure or biological sequence may be added to the video image prior to display. The position of the three-dimensional representation may correspond to the position of the identified chemical structure or biological sequence (e.g., it may be superimposed or partially superimposed). In some embodiments, the user may be provided the opportunity to interact with the three-dimensional representation. For example, the user may be able to rotate, resize, and/or relocate an added three-dimensional representation of the captured chemical structure or biological sequence as rendered upon the display. The three-dimensional representation may be rotated, for example, as a function of the position of the mobile device (e.g., tilting the device results in tilting the three-dimensional representation). The three-dimensional representation, in some embodiments, rotates automatically (e.g., slowly spinning and/or tilting upon the display).

In various embodiments, the systems, methods, and apparatus utilize or include a tablet computer, a mobile phone device, an augmented reality wearable computer, or any other computer device or system capable of capturing and presenting video data. In further embodiments, the systems, methods, and apparatus utilize or include a laptop computer, desktop computer, notebook computer or other computer device or system interfacing with a device capable of capturing and presenting video data (e.g., through a wired or wireless connection). The systems, methods, and apparatus have applications in a wide variety of industries and environments that work with graphical representations of chemical structural formulas, such as laboratories, research facilities, and classroom environments.

One aspect of the invention relates to a method including receiving video data captured by a first computing device, wherein the video data includes a video image. The method includes identifying, within the video image, by a processor of a second computing device, a graphical representation of one of a chemical structure and a biological sequence. The method also includes matching, by the processor, additional information to the graphical representation. The additional information includes at least one of (i) a three-dimensional representation of the chemical structure or biological sequence, (ii) a name of a) a chemical compound represented by the chemical structure, or b) a biological species comprising a DNA molecule, an RNA molecule, or a polypeptide represented by the biological sequence, and (iii) a plurality of properties of the chemical compound or biological species. The method also includes augmenting, by the processor, the video image with at least one of (i) at least a portion of the additional information, and (ii) one or more controls configured, upon selection, to present at least a portion of the additional information. The method further includes, after augmenting the video image, providing the video data for presentation upon a display controlled by the first computing device. The video data is presented by the first computing device in substantially real time in relation to the capture of the video data by the first computing device.

In some embodiments, the first computing device includes the second computing device. In some embodiments, the graphical representation of the chemical structure includes a two-dimensional drawing of the chemical structure. In some embodiments, augmenting the video image includes determining an orientation of the first computing device; and rendering the three-dimensional representation based in part upon the orientation of the first computing device. In some embodiments, the additional information further includes (iv) a storage location. In some embodiments, matching additional information to the graphical representation includes determining the storage location, wherein determining the storage location includes identifying the chemical compound or biological species within a catalog. In some embodiments, augmenting the video image includes rendering a first control of the one or more controls as a semi-transparent image overlaid upon the video image. In some embodiments, augmenting the video image includes superimposing the graphical representation with at least a portion of the additional information. In some embodiments, matching the additional information to the graphical representation includes comparing the graphical representation to one or more stored graphical representations. In some embodiments, matching the additional information to the graphical representation includes digitally refining the portion of the graphical representation prior to comparing the graphical representation to the one or more stored graphical representations.

In some embodiments, the method also includes receiving, by the processor, an indication of selection of a first control of the one or more controls; and augmenting, by the processor, subsequent video data with the portion of the additional information related to the first control. In some embodiments, augmenting the subsequent video data includes adding audio data to the video data, wherein the audio data includes a verbal description of the additional information.

Another aspect of the invention relates to a processor and a memory having instructions stored thereon. The instructions, when executed by the processor, cause the processor to receive video data captured by a computing device, wherein the video data includes a video image; identify, within the video image, a visual identification of a chemical structure or a biological sequence; match additional information to the visual identification. The additional information includes at least one of (i) a graphical representation of the chemical structure or biological sequence, (ii) a name of a) a chemical compound represented by the chemical structure, or b) a biological species comprising a DNA molecule, an RNA molecule, or a polypeptide represented by the biological sequence, and (iii) a plurality of properties of the chemical compound or biological species. The instructions, when executed by the processor, further cause the processor to augment the video image with at least one of (i) at least a portion of the additional information, and (ii) one or more controls configured, upon selection, to present at least a portion of the additional information. Augmenting the video image includes positionally linking the at least one of (i) the portion of the additional information and (ii) the one or more controls to the visual identification such that, upon movement of the visual identification within the video image, the at least one of (i) the portion of the additional information and (ii) the one or more controls undergo a corresponding motion. The instructions, when executed by the processor, further cause the processor to provide the video data for presentation upon a display, wherein the video data is presented in substantially real time in relation to the capture of the video data by the computing device.

In some embodiments, the computing device includes the processor. In some embodiments, the visual identification includes a two-dimensional drawing of a chemical structure or biological sequence. In some embodiments, the instructions, when executed, cause the processor to: receive, from a user of the computing device, an indication of video freeze; and responsive to the indication of video freeze, provide for presentation a still image including a most recent augmented video data frame. In some embodiments, the instructions, when executed, cause the processor to: receive, after providing the still image, selection of a first control of the one or more controls; apply, responsive to selection of the first control, the portion of the additional information related to the first control to the still image to determine a second still image; and provide, for presentation upon the display, the second still image.

Another aspect of the invention relates to a non-transitory computer readable medium having instructions stored thereon. The instructions, when executed by a processor, cause the processor to: receive video data destined for display upon a computing device, wherein the video data includes a video image; identify, within the video image, a graphical representation of one of a chemical structure and a biological sequence; match additional information to the graphical representation, wherein the additional information is arranged in a plurality of feature categories; augment the video image with one or more controls configured, upon selection, to present at least a portion of the additional information belonging to a first category of the plurality of feature categories; after augmenting the video image, provide the video data for presentation upon a display controlled by the computing device; receive, responsive to selection of a first control of the one or more controls by a user of the computing device, an indication corresponding to the first category; and responsive to the indication, augment subsequent video data with at least a portion of the additional information belonging to the first category; and after augmenting the subsequent video data, provide the subsequent video data for presentation upon the display controlled by the computing device.

In some embodiments, the computing device includes the processor. In some embodiments, the video data was captured by the computing device; and the video data is presented by the computing device in substantially real time in relation to the capture of the video data by the computing device.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

Figure 1:
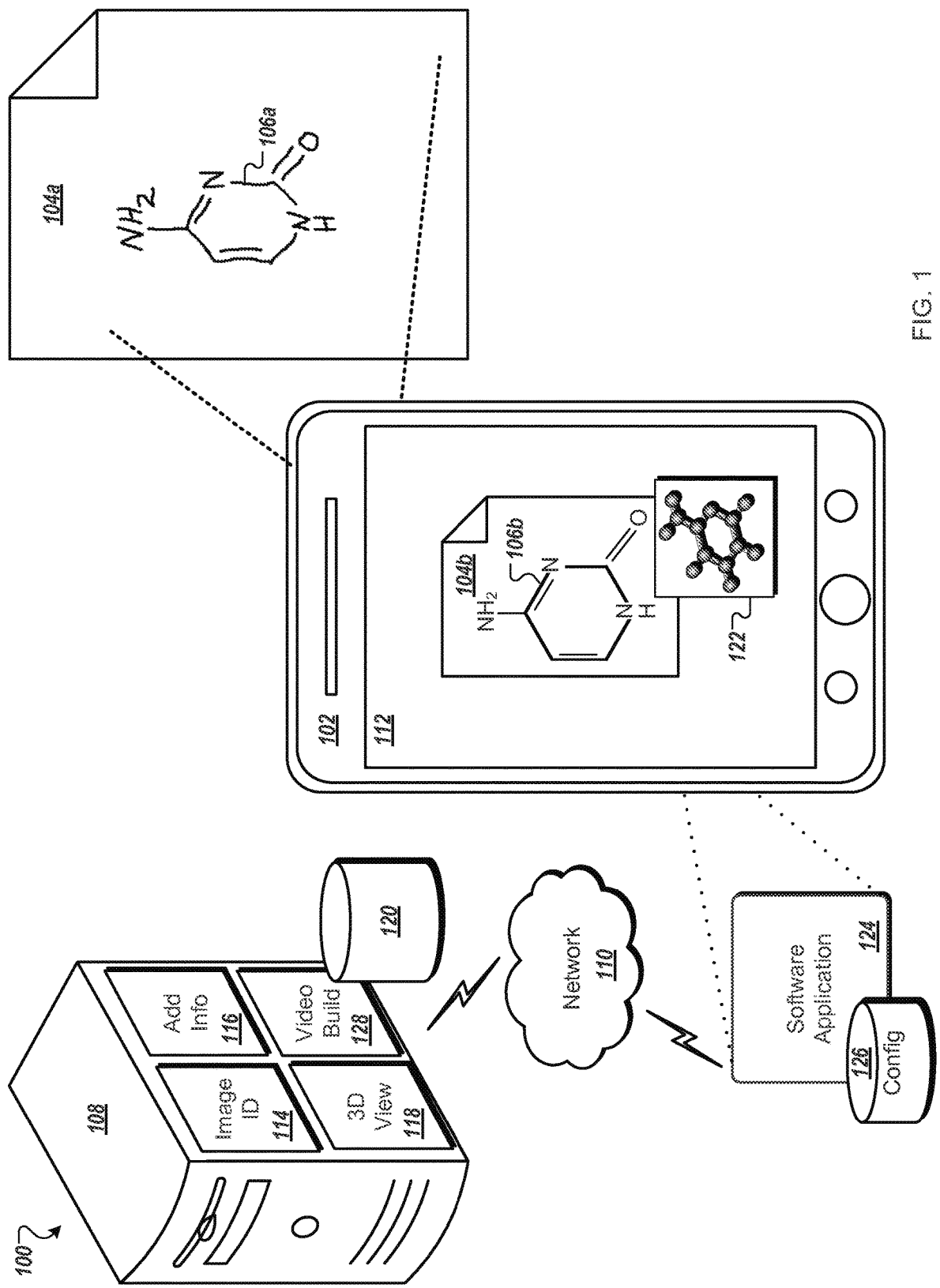
FIG. 1 is a block diagram of an example system for visually augmenting a graphical rendering of a chemical structure representation or biological sequence representation with multi-dimensional information.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

As used herein, the term "biological sequence" refers to the sequence of nucleotide or amino acid residues of a biological molecule (e.g., a DNA molecule, an RNA molecule, or a polypeptide). A biological sequence can be graphically represented in various ways, e.g., textually by a sequence of letters (e.g., using a 1-letter nucleotide code or using a 1-letter or 3-letter amino acid code), or structurally (e.g., as a chemical structure, a ball-and-stick model, a ribbon diagram, a space-filling model, or an electrostatic model).

FIG. 1 is a block diagram of an example system 100 for visually augmenting a graphical rendering of a chemical structure representation or biological sequence representation with multi-dimensional information. The system 100 includes a computing device 102 executing a software application 124 for applying augmented reality data to captured video information by identifying either a chemical structure or a biological sequence within the captured video and offering augmentation features and additional information regarding the identified chemical structure or biological sequence. The computing device 102, for example, captures a video of a chemical structure 106a drawn upon a piece of paper 104a, identifies the chemical structure 106a as being a particular chemical compound, matches additional information to the chemical compound for augmenting the video, and displays a video image 104b of the piece of paper 104a augmented with the additional information within a display area 112 of the computing device 102. The additional information, for example, includes a two-dimensional chemical structure 106b overlaying the hand-drawn chemical structure 106a and a three-dimensional graphical representation 122 of the chemical structure 106*b* presented adjacent to the two-dimensional chemical structure 106*b*.

In some embodiments, the software application 124 executing upon the computing device 102 accesses a remote server 108 (e.g., via a network 110) to conduct a portion of the operations to achieve the augmented video presented within the display 112. For example, the software application 124 executing upon the computing device 102 may pass all or a portion of the video data to the server 108. In another example, the software application 124 executing upon the computing device 102 may pass user configuration settings (e.g., as saved in a configuration data store 126), user inputs, chemical structure information, chemical compound information, biological sequence information, biological species information, or other data to the server 108. The server 108, in response, may provide data for augmenting the video data and/or an augmented video image to the computing device 102.

In some embodiments, the server 108 may include an image identification engine 114 for identifying a graphical indication of a chemical structure or biological sequence within the video data and correlating the chemical structure to a chemical compound or the biological sequence to a biological species (e.g., DNA molecule, RNA molecule, polypeptide, etc.). The chemical structure or biological sequence captured by the video data, in some examples, can include a two-dimensional graphical representation, a three-dimensional graphical representation, or another graphical indication of a chemical compound or biological species. In some embodiments, the image identification engine 114 may recognize a written name or formula of a biological species or chemical compound within the video data. The chemical structure or biological sequence captured within the video data, in some additional examples, may be illustrated or hand-drawn on a flat or curved surface such as, in some examples, a white board, chalk board, or transparent hood of a laboratory experiment station.

In some embodiments, the server 108 may include an additional information matching engine 116 for matching additional information to the identified chemical compound or biological species, such as, in some examples, a name of the chemical compound or biological species, properties of the chemical compound or biological species, or a graphical representation (e.g., two dimensional, three dimensional, etc.) of the chemical structure or biological sequence. In some implementations, the additional information includes a location of the chemical compound or biological species within a laboratory, or reaction information regarding an ongoing experiment involving the chemical structure or biological sequence. The additional information, in some implementations, is accessed by the additional information matching engine 116 from one or more databases, such as a data store 120. In some implementations, a portion of the additional information is accessed from a public repository, such as the PubChem Compound database maintained by the National Center for Biotechnology Information (NCBI), the molecular spectral databases maintained by the National Institute of Standards and Technology (NIST), the Genbank sequence database maintained by NCBI, or the UniProt protein sequence database maintained by the UniProt consortium. In some implementations, a portion of the additional information is accessed from an electronic lab notebook (ELN) system.

The server 108, in some implementations, includes a three-dimensional view engine 118 for presenting and adjusting a three-dimensional graphical representation of the identified chemical compound or biological species. The three-dimensional view engine 118, for example, may be used to render the three-dimensional graphical representation 122 within the display 112. In some embodiments, the three-dimensional view engine 118 modifies the orientation of the three-dimensional graphical representation 122 based upon orientation input, such as a direct user input (e.g., one or more controls linked to the three-dimensional graphical representation 122 for rotating or tilting the aspect of the three-dimensional graphical representation 122) or device orientation input (e.g., as gleaned from one or more orientation sensors of the computing device 102 such as a gyroscope or accelerometer).

In some embodiments, the server 108 includes a video augmenting engine 128 for building an augmented video for presentation within the display 112. The video augmenting engine 128, for example, may merge the video captured by the computing device 102 with augmentation data such as, in some examples, a portion of the additional information (e.g., obtained at least in part from the data store 120), selectable controls for presenting additional information, and/or a two-dimensional or three-dimensional graphical representation of the chemical structure or biological sequence. In some embodiments, the video augmenting engine 128 presents a portion of the augmentation data as semi-transparent images overlaying the original video image. For example, the hand-drawn chemical structure 106*a* may be partially visible beneath the two-dimensional chemical structure 106*b*. The video augmenting engine 128, in some implementations, presents a portion of the augmentation data in a manner that "pins" the augmentation data to the video image of the chemical structure 106*a*. For example, should the user move the computing device 102 or the paper 104 such that the alignment of the chemical structure 106*a* moves within the display 112, a portion of the augmentation data may move with the position of the chemical structure 106*a* within the video image. Visual elements, in some embodiments, may tie the portion of the augmentation data to the chemical structure 106*a*. For example, arrows, call-out boxes, or lead lines may create a visual connection between the augmentation data and the chemical structure 106*b*. This may be especially useful, for example, if two or more chemical structures or biological sequences are illustrated within the video data of the display 112. In this manner, the user could immediately interpret which augmentation data belonged to which chemical structure or biological sequence.

In addition to presenting the three-dimensional graphical representation 122 and overlaying the hand-drawn chemical structure 106*a* with the two-dimensional chemical structure 106*b*, in some implementations, the software application 124 may be used to provide the user with multi-dimensional data regarding the chemical structure 106. For example, the software application 124 may be configured to present a first set of options (e.g., as a default or based upon the user configuration settings in the configuration store 126) as one or more selectable controls (not illustrated), each control representing a category of information related to the chemical structure 106. In some examples, the categories may include chemical properties, a storage location, or a name of the compound. Upon selecting a first selectable control, the software application 124 may update the augmentation data presented within the display 112 to include information identified as pertaining to the selected category. The information, in some examples, may include text, graphics, video, and/or audio information. In some embodiments, one or more sub-categories may be presented to the user upon selection of a primary category. For example, upon selection of a properties category, sub-categories of physical properties and chemical properties may be presented. In this manner, a user may drill down to obtain more and more specific information regarding the chemical structure 106.

Although illustrated in a particular example system 100, in other implementations, the computing device 102, shown here as a handheld computing device, may be a tablet computer, laptop computer, desktop computer, an augmented reality wearable computer such as computerized glasses (e.g., Google® Glass™ by Google® Inc. of Mountain View, Calif.), or other computing device in communication with a video capture device and a display.

Additionally, in other implementations, one or more of the image identification engine 114, additional information matching engine 116, three-dimensional view engine 118, and video augmenting engine 128 may reside within the computing device 102 (e.g., as part of the software application 124). In some implementations, the server 108 may include two or more servers, such as a server farm or cloud computing service for video augmentation. Further details and options for providing methods and systems for visually augmenting a graphical rendering of either a chemical structure representation or a biological sequence representation with multi-dimensional information are described below.

Figure 2:
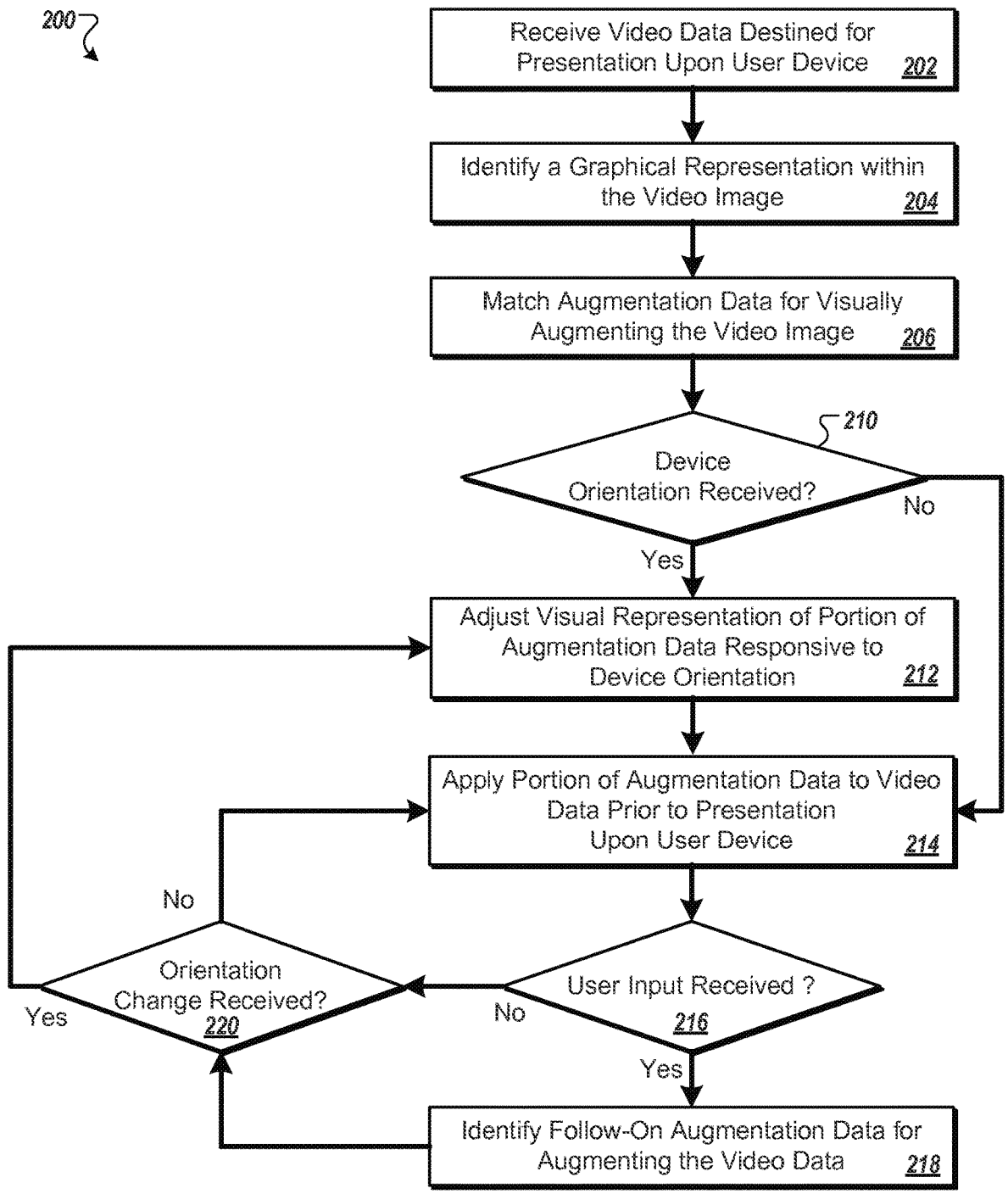
FIG. 2 is a flow chart of an example method for visually augmenting a graphical rendering of a chemical structure representation or biological sequence representation with multi-dimensional information.

FIG. 2 is a flow chart of an example method 200 for visually augmenting a graphical rendering of a chemical structure representation with multi-dimensional information. The method 200, in some implementations, may be performed by the server 108 and/or the software application 124, as described in relation to FIG. 1.

In some implementations, the method 200 begins with receiving video data destined for presentation upon a user device (202). The video data, for example, may be captured using a camera feature of computerized eye glasses or a handheld computing device such as the computing device 102 described in relation to FIG. 1. In other examples, the video data may be captured using a video camera device connected to a personal computer, or the video data may be provided in real time from a separate computing device (e.g., broadcast a number of students' computing devices in a lecture hall). The video includes a video image track. In some implementations, the video data further includes an audio image track and/or a metadata track.

In some implementations, a graphical representation of either a chemical structure or a biological sequence is identified within the video image track of the video data (204). The graphical representation, for example, may be identified by the image identification engine 114, described in relation to FIG. 1. The chemical structure or biological sequence, for example, may be a hand-drawn illustration or print illustration representing a chemical compound or biological species. In some implementations, the chemical structure or biological sequence may be partially presented (e.g., one or more bonds missing, a portion of an atom identifier cut off), obscured, or presented upon a curved surface. If the chemical structure or biological sequence is not complete or otherwise exactly matching a corresponding chemical compound or biological species, in some implementations, the chemical compound or biological species is digitally refined to obtain an image for comparison with known chemical structures or biological sequences. For example, once a suspected chemical structure or biological sequence has been identified, the portion of the image containing the suspected chemical structure may be pruned (e.g., stray lines or text removed), image-adjusted, or otherwise digitally altered in an attempt to match the graphical representation of the chemical structure or biological sequence captured within the video image to a chemical known chemical compound or biological species. In a particular example, two or more video frames may be reviewed (e.g., merged, appended) in relation to each other to identify the chemical compound or biological species.

In other implementations, rather than identifying a graphical representation of a chemical structure or biological sequence, a name of a chemical compound or biological species, a chemical formula, or another representation of a chemical compound or biological species may be identified.

In some implementations, augmentation data is matched to the chemical compound or biological species to augment the video image (206). The augmentation data may be matched to the chemical compound or biological species, for example, by the additional information matching engine 116 described in relation to FIG. 1. The augmentation data, in some implementations, includes image data such as a two-dimensional or three-dimensional representation of the chemical structure or biological sequence. In some implementations, the augmentation data includes additional information such as properties of the chemical compound or biological species, a storage location of the chemical compound or biological species, or reaction information regarding an experiment involving the chemical compound or biological species. The additional information, for example, may be arranged in categories and sub-categories such that a user may drill down to obtain further details regarding the chemical compound or biological sequence. To aid in obtaining the additional information, in some implementations, the augmentation data includes control information such as one or more selectable call-out boxes configured, upon selection, to present a portion of the additional information.

In some implementations, an indication of device orientation is received (210). For example, data derived from an orientation sensor (e.g., gyroscope, accelerometer, etc.) of a handheld computing device may be provided to aid in the augmentation of the video data. If the device orientation is known (210), in some implementations, a visual representation of a portion of the additional information is adjusted responsive to the device orientation (212). For example, the orientation of text presented as additional information or written upon a selectable control may be adjusted. If a three-dimensional graphical representation of the chemical structure or biological sequence has been identified as augmentation data, in some implementations, a rotation and/or revolution of the three-dimensional graphical representation may be adjusted based upon the orientation of the device. For example, the three-dimensional graphical representation may tilt with the tilting of the handheld device. The orientation of the three-dimensional graphical representation may be adjusted, for example, by the three-dimensional view engine 118, described in relation to FIG. 1.

In some implementations, a portion of the augmentation data is applied to the video data prior to presentation upon the user device (214). The augmentation data may be applied to the video data, for example, by the video augmenting engine 128, described in relation to FIG. 1. The video data, for example, may be merged with the augmentation data to create an augmented video data for presentation by the user device. In some embodiments, a portion of the augmentation data is presented as semi-transparent images overlaying the original video image. In some implementations, a portion of the augmentation data is presented in a manner that "pins" the augmentation data to the graphical representation of the chemical structure or biological sequence. For example, should the user move the computing device or the item including the graphical representation of the chemical structure or biological sequence such that the alignment of the chemical structure or biological sequence moves within the video image frame, a portion of the augmentation data may move with the position of the graphical representation of the chemical structure or biological sequence. Visual elements, in some embodiments, may tie a portion of the augmentation data to the graphical representation of the chemical structure or biological sequence. For example, arrows, call-out boxes, or lead lines may create a visual connection between the augmentation data and the graphical representation of the chemical structure or biological sequence.

In some implementations, user input may be received (216). For example, a user may select one of the selectable controls presented as augmentation data, or a user may interact with a user-selectable three-dimensional graphical representation of the chemical structure or biological sequence presented as augmentation data. If a user input other than orientation change is received (216), in some implementations, follow-on augmentation data is identified for augmenting the video data (218). For example, based upon the selection by the user of a category of additional information, corresponding image, text, and/or graphic data may be presented upon the video feed as augmentation data. Using the same example, rather than or in addition to the additional information, the user may be presented with one or more selectable sub-categories related to the selected category.

Whether or not follow-on augmentation data is identified, in some implementations, it is determined whether an orientation change has been received (220). In some implementations, the user alters the orientation of the computing device (e.g., physically tilts the device or rotates the display), causing updated orientation information to be received. In some implementations, the user manipulates the three-dimensional graphical representation of the chemical structure or biological sequence, causing orientation data specific to the three-dimensional graphical representation to be received. The visual representation of at least a portion of the augmentation data, in some implementations, is adjusted responsive to the orientation change (212).

Whether or not an orientation change was received at step 220, as described previously in relation to step (214), in some implementations, the augmentation data (and/or, if applicable, follow-on augmentation data) is applied to the subsequent (e.g., current) video data prior to presentation of the augmented subsequent video data upon the user device (214). The method 200, in some implementations, continues to update and adjust as additional video data frames, user inputs, and orientation changes are received.

Although described in relation to a series of particular steps, in some implementations, one or more of the steps of the method 200 may be performed in a different order, or one or more steps may be performed in parallel. In some implementations, one or more of the steps of the method 200 may be removed or modified, or one or more steps may be added to the method 200, while staying within the scope and intent of the method 200.

Figure 3:
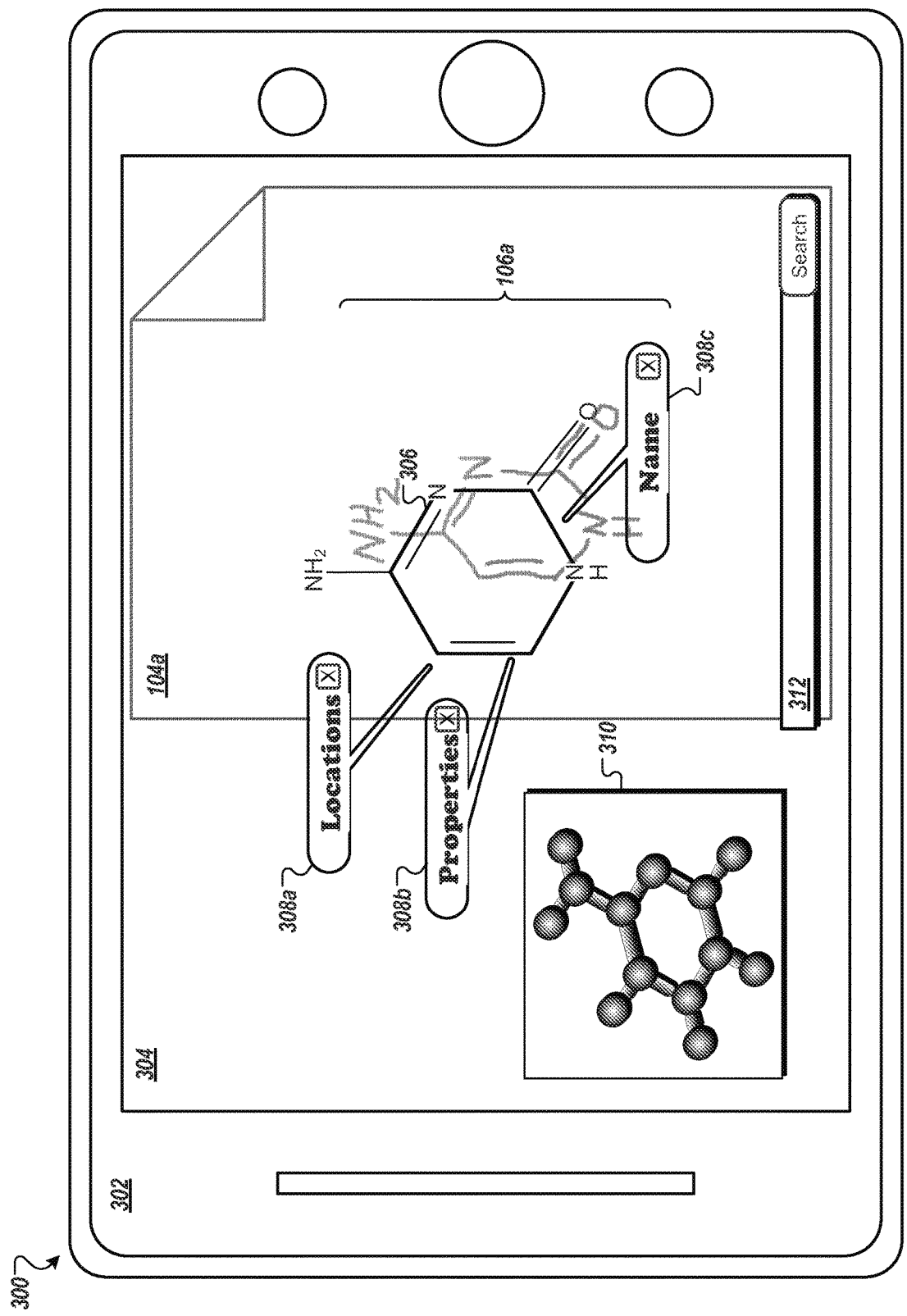
FIG. 3 is a screen shot of an example user interface demonstrating visual augmentation of a graphical rendering of a chemical structure representation.

FIG. 3 is a screen shot 300 of an example user interface 304, rendered upon a computing device 302. The user interface 304 demonstrates an example of visual augmentation of a graphical rendering of a chemical structure representation. The user interface 304, for example, may be presented in relation to capturing video data regarding the hand-drawn chemical structure 106a upon the paper 104a, as described in relation to FIG. 1.

As illustrated within the user interface 304, the image of the paper 104a containing the hand-drawn chemical structure 106a has been obscured by semi-transparent augmentation data, including a two-dimensional graphical representation 306 of the chemical structure 106a and a series of selectable call-out boxes 308 identifying categories of additional information pertaining to the chemical structure 106a such as a locations category call-out box 308a, a properties category call-out box 308b, and a name category call-out box 308c. Upon selection by a user of one of the selectable call-out boxes 308, for example, augmentation data regarding the selected category may be presented to the user in the display area of the computing device 302. In some implementations, upon selection by a user of one of the selectable call-out boxes 308, one or more additional controls are presented to the user. The additional controls, for example, may be configured to present, upon selection, information regarding one or more sub-categories of the identified category.

In some implementations, the one or more additional controls may include a control configured to allow the user to freeze the video image containing the information regarding the identified category. For example, upon being presented with information relevant to the identified chemical structure or biological sequence, the user may desire to take a "snapshot" of the information for review without having to maintain video connection with the identified chemical structure or biological sequence (e.g., move the camera lens of the computing device 102 away from pointing at the paper 104a). In some implementations, although the video has been frozen on a snapshot image (e.g., current frame), the controls remain active for pursuing additional information regarding the chemical structure or biological sequence illustrated within the snapshot image.

The user interface 304 also includes a three-dimensional graphical representation 310 of the chemical structure 106a, presented adjacent to the two-dimensional graphical representation 306. In some implementations, upon changing the orientation of the computing device 302, the orientation of the three-dimensional graphical representation 310 may automatically adjust (e.g., tilt or rotate). In some implementations, the three-dimensional graphical representation 306 slowly revolves and/or rotates as a moving image within the video presented by the user interface 304.

At the bottom of the user interface 304, a search field 312 is presented. The search field 312 may be used, for example, for searching for additional information related to the chemical structure 106a.

Figure 4:
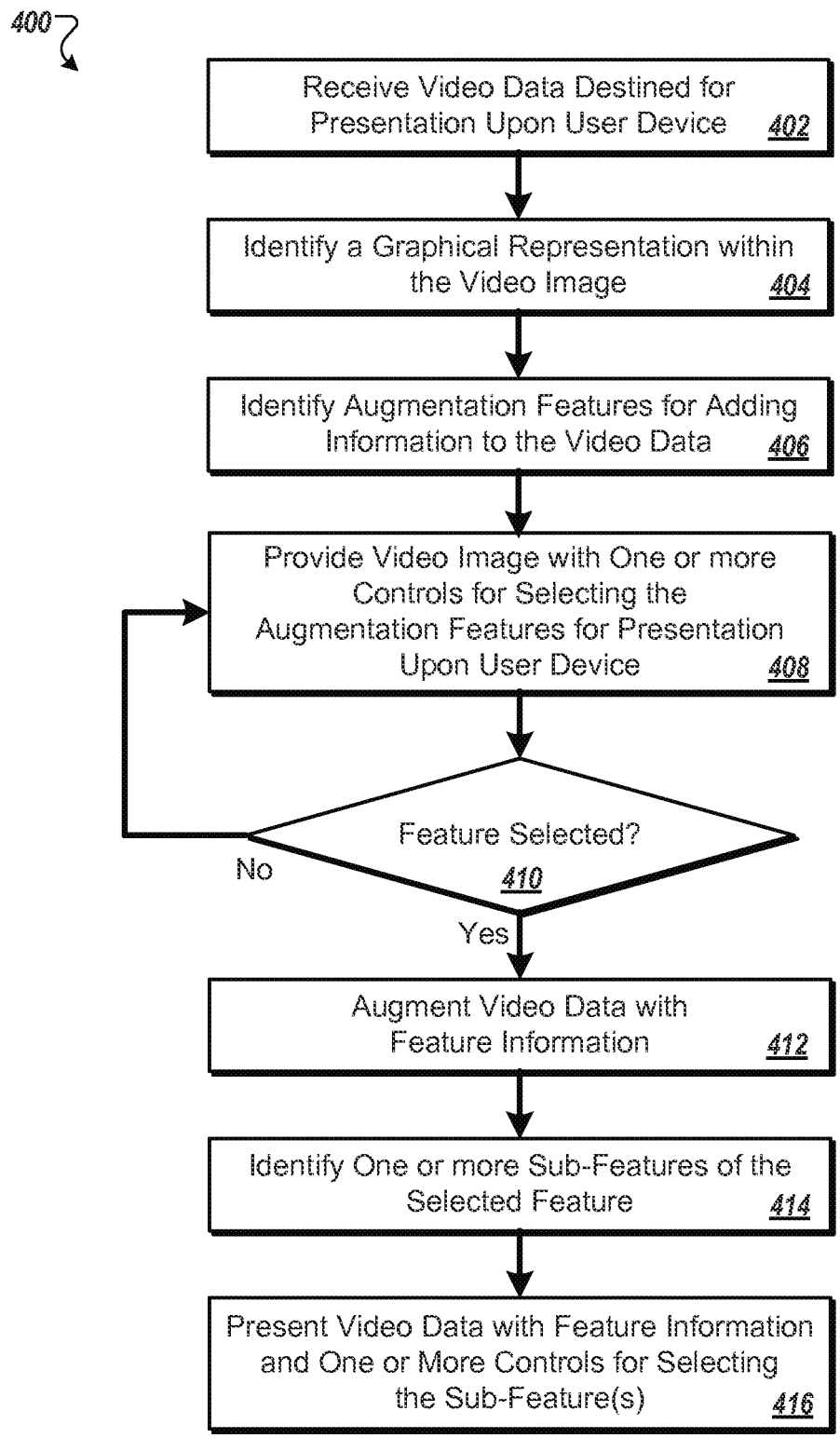
FIG. 4 is a flow chart of an example method for deriving and presenting multi-dimensional information related to a graphical rendering of a chemical structure representation or biological sequence representation.

FIG. 4 is a flow chart of an example method 400 for deriving and presenting multi-dimensional information related to a graphical rendering of a chemical structure representation or biological sequence representation. The method 400, in some implementations, may be performed by the server 108 and/or the software application 124, as described in relation to FIG. 1.

In some implementations, the method 400 begins with receiving video data destined for presentation upon a user device (402). The video data, for example, may be captured using a camera feature of computerized eye glasses or a handheld computing device such as the computing device 102 described in relation to FIG. 1. In other examples, the video data may be captured using a video camera device connected to a personal computer, or the video data may be provided in real time from a separate computing device (e.g., broadcast a number of students' computing devices in a lecture hall). The video includes a video image track. In some implementations, the video further includes an audio image track and/or a metadata track.

In some implementations, a graphical representation of either a chemical structure or a biological sequence is identified within the video image track of the video data (404). The graphical representation, for example, may be identified by the image identification engine 114, described in relation to FIG. 1. The chemical structure or biological sequence, for example, may be a hand-drawn illustration or print illustration representing a chemical formula or biological species. In some implementations, the chemical structure or biological sequence may be partially presented (e.g., one or more bonds missing, a portion of an atom identifier cut off), obscured, or presented upon a curved surface. If the chemical structure or biological sequence is not complete or otherwise exactly matching a corresponding chemical compound or biological species, in some implementations, the chemical compound or biological species is digitally refined to obtain an image for comparison with known chemical structures or biological sequences. For example, once a suspected chemical structure or biological sequence has been identified, the portion of the image containing the suspected chemical structure may be pruned (e.g., stray lines or text removed), image-adjusted, or otherwise digitally altered in an attempt to match the graphical representation of the chemical structure or biological sequence captured within the video image to a chemical known chemical compound or biological species. In a particular example, two or more video frames may be reviewed (e.g., merged, appended) in relation to each other to identify the chemical compound or biological species.

In other implementations, rather than identifying a graphical representation of a chemical structure or biological sequence, a name of a chemical compound or biological species, a chemical formula, or another representation of a chemical compound or biological species may be identified.

In some implementations, augmentation features are identified for adding information related to the chemical compound or biological species to the video data (406). The augmentation features may be identified, for example, by the additional information matching engine 116 described in relation to FIG. 1. The augmentation features, for example, may be arranged in categories and sub-categories such that a user may drill down to obtain further details regarding the chemical compound or biological species. To aid in obtaining the additional information, in some implementations, each augmentation feature is associated with a user interface control configured, upon selection, to present category information related to the chemical compound or biological species.

In some implementations, the video image, including one or more controls for selecting the augmentation features, is provided for presentation to the user on the user computing device (408). The controls, in some examples, may include any combination of call-out boxes, radio buttons, a configuration listing, a search box, or a voice activated listing of available options for further information. In some implementations, the controls are pinned to the identified chemical structure or biological sequence, such that, as the identified chemical structure or biological sequence moves within the display region of the user computing device (e.g., due to movement of the camera relative to the chemical structure or biological sequence being captured) the controls move within the display to be positioned relative to the identified chemical structure or biological sequence. In some implementations, one or more controls are made visible or rendered opaque upon initial input from a user (e.g., identification of a touch by the user upon a touch screen display, identification of a "click" by the user via an input tool, etc.).

In some implementations, if a feature is selected by the user (410), the video data is augmented with information related to the selected feature (412). For example, upon receiving an indication of a selection of a particular control, information related to that control (e.g., one or more of text, graphic, video, and audio information) may be applied to subsequent video data prior to presentation of the subsequent video data.

In some implementations, in lieu of or in addition to presenting information related to the selected control, one or more sub-features of the selected features are identified (414). For example, one or more sub-categories may be identified related to a selected information category. Upon identification of the sub-categories, in some implementations, the video data may be augmented with one or more controls for selecting the one or more sub-categories. If, instead, no sub-categories are available (e.g., the user has reached the finest granularity of information regarding the current topic), in some implementations, one or more controls regarding a higher level of category abstraction may be presented (e.g., akin to a "back" or "related information" option).

In some implementations, the augmented subsequent video data is presented with feature information and/or one or more controls for selecting sub-features of the identified feature (416). The augmented subsequent video data, for example, may be presented in a manner similar to that described in relation to step 408.

Although described in relation to a series of particular steps, in some implementations, one or more of the steps of the method 400 may be performed in a different order, or one or more steps may be performed in parallel. In some implementations, one or more of the steps of the method 400 may be removed or modified, or one or more steps may be added to the method 400, while staying within the scope and intent of the method 400.

Figure 5:
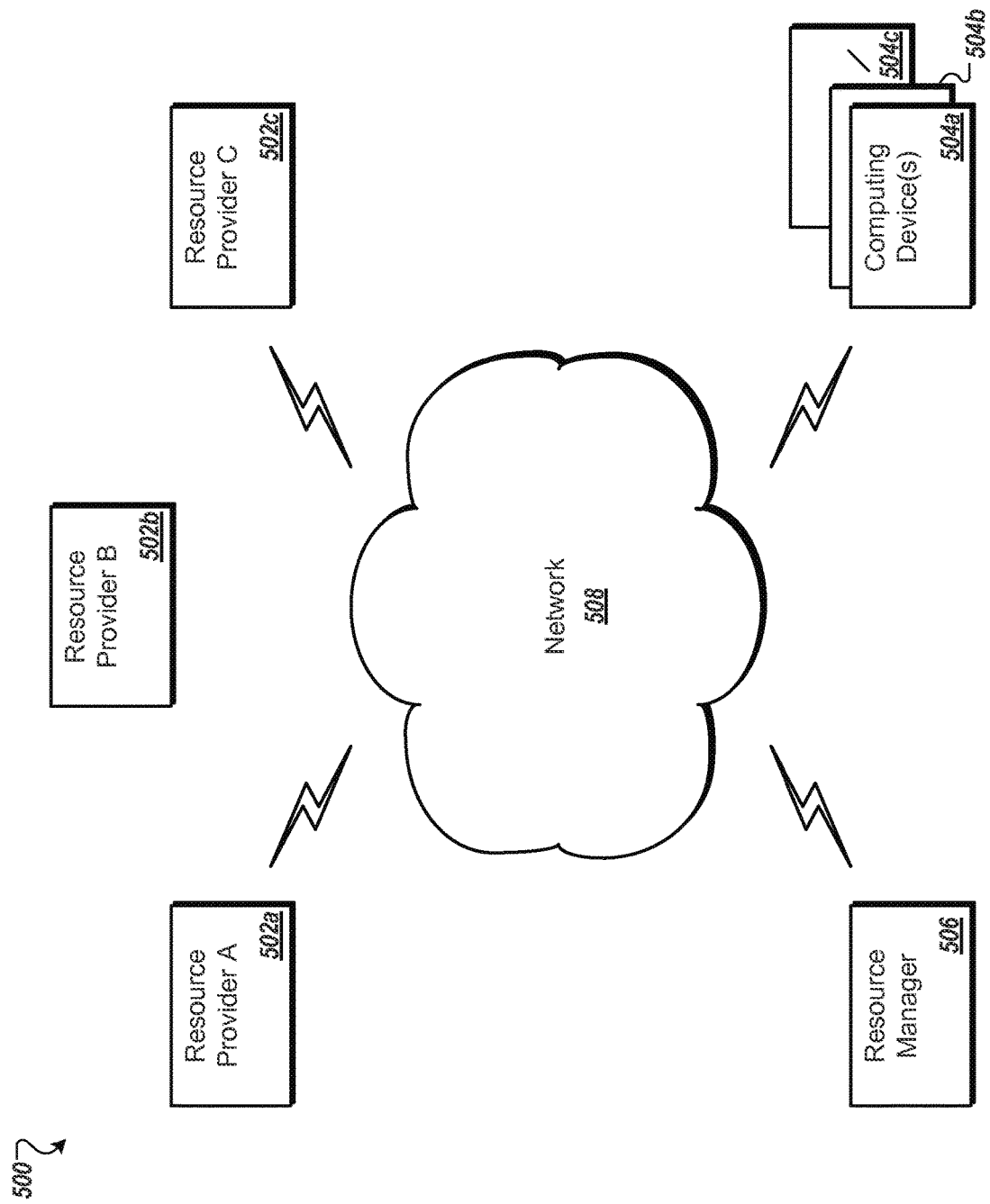
FIG. 5 is a block diagram of an example network environment for visually augmenting a graphical rendering of a chemical structure representation with multi-dimensional information.

As shown in FIG. 5, an implementation of an exemplary cloud computing environment 500 for visually augmenting a graphical rendering of either a chemical structure representation or a biological sequence representation with multidimensional information is shown and described. The cloud computing environment 500 may include one or more resource providers 502a, 502b, 502c (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504a, 504b, 504c (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
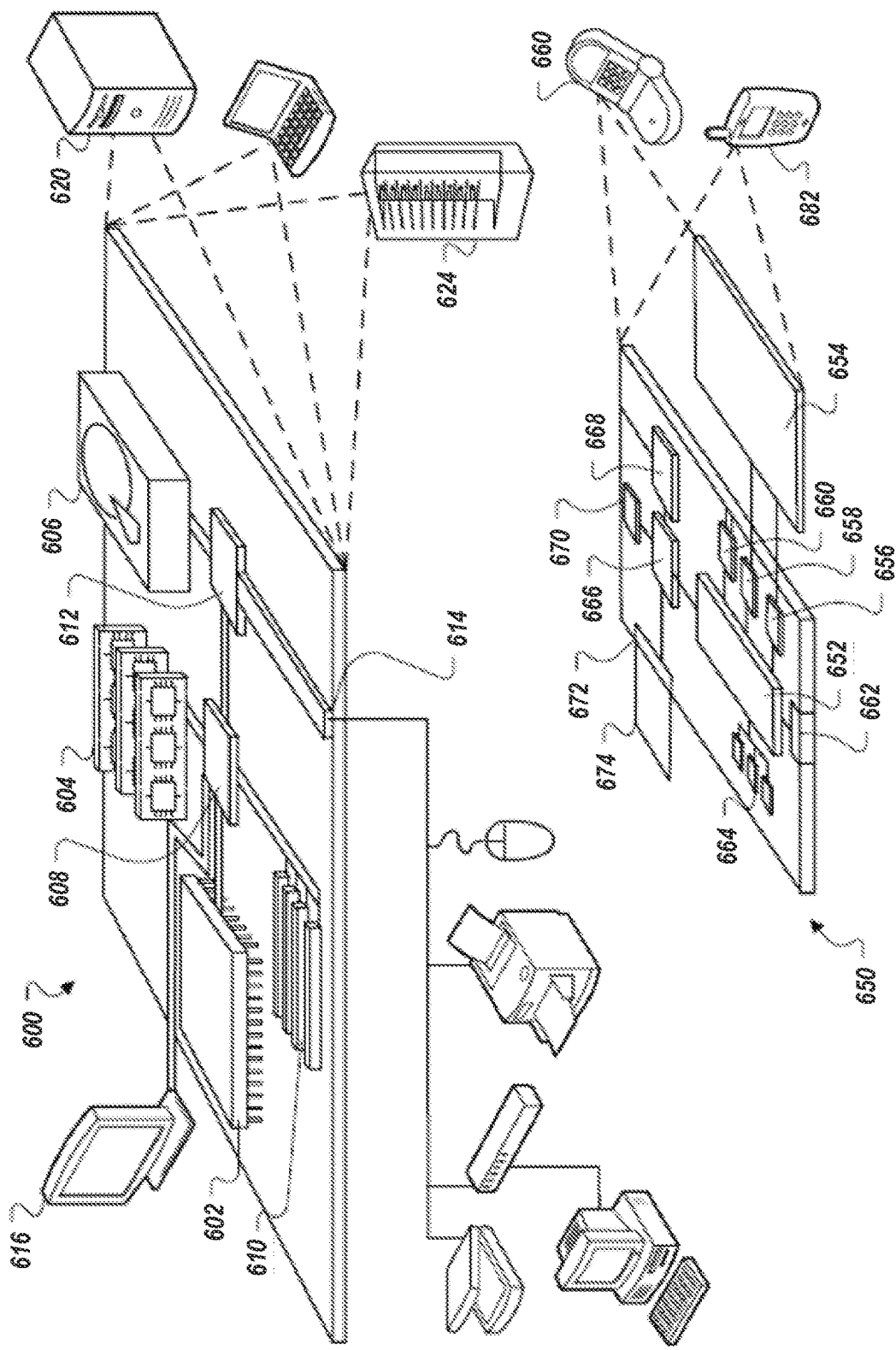
FIG. 6 is a block diagram of an example computing device and an example mobile computing device.

FIG. 6 shows an example of a computing device 600 and a mobile computing device 650 that can be used to implement the techniques described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

It should also be noted that embodiments of the present disclosure may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or Java. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

In view of the structure, functions and apparatus of the systems and methods described here, in some implementations, systems and methods for visually augmenting a graphical rendering of a chemical structure representation with multi-dimensional information are provided. Having described certain implementations of visual augmentation of a graphical rendering of a chemical structure representation or biological sequence representation with multi-dimensional information, it will now become apparent to one of skill in the art that other implementations incorporating the concepts of the disclosure may be used. Therefore, the disclosure should not be limited to certain implementations, but rather should be limited only by the spirit and scope of the following claims.

The invention claimed is:

1. A method comprising:
receiving a live video feed comprising two or more video frames captured by a single video camera;
digitally altering, based on a review of the two or more video frames together from the live video feed, at least a portion of the live video feed in order to match a graphical representation of either a chemical structure or biological sequence captured within the two or more video frames to a known chemical compound or biological species, wherein the review of the two or more video frames together from the live video feed comprises:
merging of the two or more video frames from the live video feed; or
appending of one of the two or more video frames from the live video feed to another one of the two or more video frames from the live video feed;
automatically identifying, within the digitally altered live video feed, by a processor of a computing device, an identifier of a chemical compound or a biological species;
querying, by the processor, a database for additional information associated with the chemical compound or biological species;
rendering, by the processor, augmentation data corresponding to the additional information;
generating an output video feed by graphically merging live video feed with the augmentation data, wherein the graphically merging comprises positionally linking the augmentation data with the identifier in the output video feed; and
outputting the output video feed for display in substantially real time in relation to the live video feed.

2. The method of claim 1, wherein the identifier is a written name or formula of the chemical compound or the biological species.

3. The method of claim 1, wherein the identifier is written on a curved surface.

4. The method of claim 1, wherein the additional information comprises one or more of a two-dimensional representation of the identified chemical compound or biological species, a three-dimensional representation of the chemical compound or biological species, or a property of the chemical compound or biological species.

5. The method of claim 1, wherein the additional information further comprises one or more of:
a storage location of the chemical compound or the biological species; or
information regarding ongoing experiment(s) with use of the chemical compound or the biological species.

6. The method of claim 1, wherein the augmentation data comprises one or more of graphics corresponding to at least a portion of the additional information, or one or more graphical controls which presents at least a portion of the additional information upon selection.

7. The method of claim 6, wherein the rendering and the graphically merging comprises rendering a first graphical control of the one or more graphical controls as a semi-transparent image and overlaying the semi-transparent image upon the live video feed.

8. The method of claim 1, wherein the rendered augmentation data is one or more of:
a two-dimensional representation of the chemical compound or the biological species; or
a three-dimensional representation of the chemical compound or the biological species.

9. The method of claim 8, wherein graphically merging the received live video feed with the rendered augmentation data comprises superimposing the two-dimensional representation of the chemical compound or the biological species or the three-dimensional representation of the chemical compound or the biological species with at least a portion of the additional information.

10. The method of claim 8, wherein the two-dimensional representation of the chemical compound or the biological species and the three-dimensional representation of the chemical compound or the biological species are graphical representations of the chemical compound or the biological species.

11. The method of claim 10, wherein, a graphical representation of the graphical representations of the chemical compound or the biological species is partially obscured, wherein one or more bonds is missing or wherein a portion of an atom identifier is missing.

12. The method of claim 1, wherein the computing device includes the video camera.

13. The method of claim 1, wherein the live video feed comprises a sequence of images.

14. A system comprising:
a processor: and
a memory having instructions stored thereon, wherein the instructions, when executed by the processor, cause the processor to:
receive a live video feed comprising two or more video frames captured by a single video camera;
digitally alter, based on a review of the two or more video frames together from the live video feed, at least a portion of the live video feed in order to match a graphical representation of either a chemical structure or biological sequence captured within the two or more video frames to a known chemical compound or biological species, wherein the review of the two or more video frames together from the live video feed comprises:
merging of the two or more video frames from the live video feed; or
appending of one of the two or more video frames from the live video feed to another one of the two or more video frames from the live video feed;
automatically identify, within the digitally altered live video feed, by a processor of a computing device, an identifier of a chemical compound or a biological species;
query a database for additional information associated with the chemical compound or biological species;
render augmentation data corresponding to the additional information;
generate an output video feed by graphically merging the received live video feed with the augmentation data, wherein the graphically merging comprises positionally linking the augmentation data with the identifier in the output video feed; and
output the output video feed for display in substantially real time in relation to the live video feed.

15. The system of claim 14, wherein the identifier is a written name or formula of the chemical compound or the biological species.

16. The system of claim 14, wherein the rendered augmentation data comprises one or more of graphics corresponding to at least a portion of the additional information, or one or more graphical controls which presents at least a portion of the additional information upon selection.

17. The system of claim 16, wherein the rendering and the graphically merging comprises rendering a first graphical control of the one or more graphical controls as a semi-transparent image and overlaying the semi-transparent image upon the live video feed.

18. The system of claim 14, wherein the rendered augmentation data is one or more of:
a two-dimensional representation of the chemical compound or the biological species; or
a three-dimensional representation of the chemical compound or the biological species.

19. The system of claim 18, wherein the graphically merging the received live video feed with the rendered augmentation data comprises superimposing the two-dimensional representation of the chemical compound or the biological species or the three-dimensional representation of the chemical compound or the biological species with at least a portion of the additional information.

20. The system of claim 18, wherein the two-dimensional representation of the chemical compound or the biological species and the three-dimensional representation of the chemical compound or the biological species are graphical representations of the chemical compound or the biological species.

21. The system of claim 14, wherein the computing device includes the video camera.

22. The system of claim 14, wherein the live video feed comprises a sequence of images.

* * * * *